United States Patent
Calino

[19]

[11] Patent Number: 6,032,930

[45] Date of Patent: Mar. 7, 2000

[54] AUTOMATIC AIR FRESHENING SYSTEM

[76] Inventor: Jay Cee Calino, 1841 Oates Dr. #1113, Mesquite, Tex. 75150

[21] Appl. No.: 09/080,711

[22] Filed: May 18, 1998

[51] Int. Cl.[7] ........................................ B01F 3/04
[52] U.S. Cl. .................... 261/26; 261/104; 261/DIG. 17; 261/DIG. 65; 422/124
[58] Field of Search ................... 261/100, 107, 261/DIG. 65, 26, DIG. 17, 104; 422/124, 123; 454/156; 239/53, 54, 55, 56, 57, 58, 59, 60

[56] References Cited

U.S. PATENT DOCUMENTS

| | | | |
|---|---|---|---|
| 3,633,881 | 1/1972 | Yurdin | 261/24 |
| 3,872,280 | 3/1975 | Van Dalen | 422/124 |
| 4,603,030 | 7/1986 | McCarthy | 422/4 |
| 4,743,406 | 5/1988 | Steiner et al. | 261/30 |
| 4,808,347 | 2/1989 | Dawn | 261/30 |
| 4,968,456 | 11/1990 | Muderlak et al. | 261/30 |
| 5,240,653 | 8/1993 | RamKissoon | 261/DIG. 65 |
| 5,431,885 | 7/1995 | Zlotnik et al. | 422/124 |
| 5,498,397 | 3/1996 | Horng | 422/124 |
| 5,567,361 | 10/1996 | Harper | 261/26 |
| 5,698,166 | 12/1997 | Vick | 422/124 |
| 5,704,832 | 1/1998 | Borrell | 454/157 |
| 5,833,929 | 11/1998 | Watson et al. | 422/123 |

FOREIGN PATENT DOCUMENTS

| | | | |
|---|---|---|---|
| 2222775 | 3/1990 | United Kingdom | 422/124 |

*Primary Examiner*—David A. Simmons
*Assistant Examiner*—Robert Hopkins
*Attorney, Agent, or Firm*—Rudolf O. Siegesmund

[57] ABSTRACT

An automatic air scenting system that introduces a variety of pre-selectable scents into the heating/air-conditioning duct of a motor vehicle or habitable structure comprising a perforated housing, an electric fan for drawing air through the perforated housing, a container of compressed fiber blocks soaked in a scented oil based liquid positioned within the perforated housing, and a hose connecting the housing to the duct of the heating/air conditioning system whereby the fan forces the accumulated scent through the hose into the duct. Automatic functioning is obtained by connecting the fan power lines to the on/off switch and thermostat wiring of the heating/air-conditioning system.

6 Claims, 2 Drawing Sheets

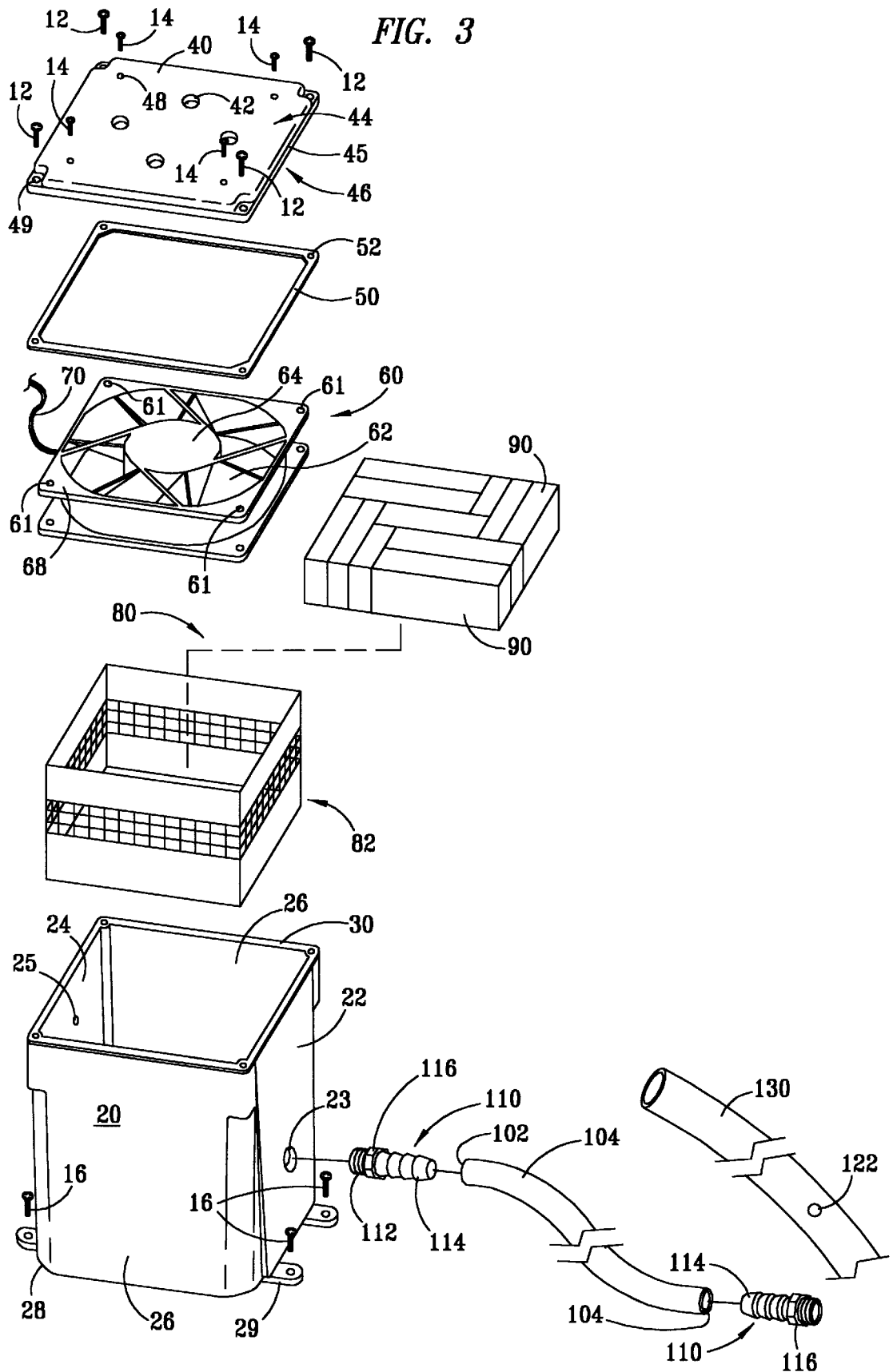

AUTOMATIC AIR FRESHENING SYSTEM

FIELD OF THE INVENTION

The present invention is directed, in general, to an apparatus for introducing a selectable variety of scents into the heating/air conditioning duct of a motor vehicle or habitable structure.

BACKGROUND OF THE INVENTION

The present invention relates to inventions for introducing a pre-selectable scent into the air within a motor vehicle or habitable structure by accumulating fragrance from blocks of compressed fiber soaked in a a scented oil based liquid positioned within a perforated housing and forcing the scented air through a connecting hose into the duct of the motor vehicle or habitable structure's heating air-conditioning system by means of a electric fan within the perforated housing unit.

The use of various apparatus to introduce scent into the air is well known in the prior art. Various types of air freshening or deodorizing devices have been utilized for inducing air flow past a product which may be vaporized, either by evaporation or sublimation, in order to distribute the vaporized product throughout the surrounding environment. For example, U.S. Pat. No. 5,704,832 to Borrell discloses an air-conditioning vent cover with an attached propellor device for introducing fragrance into the air of a room. U.S. Pat. No. 5,698,166 to Vick discloses a device for scenting air by affixing an air-permeable substrate with a solid fragrant residue on the substrate to the air filter of an air-conditioning system. U.S. Pat. No. 5,567,361 to Harper discloses a fragrance enhancer with an external power supply that accumulates fragrance and forces it through vent holes in the device by means of air driven by a fan. U.S. Pat. No. 5,498,397 to Horng discloses a battery operated system for introducing the aroma of spices directly into the surrounding air. U.S. Pat. No. 5,431,885 to Zlotnick et. al. discloses a device for releasing fragrance into the surrounding air. U.S. Pat. No. 4,968,456 to Muderlak et. al. discloses a fan driven air freshener for insertion into the cigarette lighter of a motor vehicle. U.S. Pat. No. 4,808,347 to Dawn discloses a device for introducing scent directly into the air of room within which the device is positioned. U.S. Pat. No. 4,743,406 to Steiner et. al. discloses a battery powered self contained air freshener. U.S. Pat. 4,603,030 to McCarthy discloses a system for directing at least two different scents toward at least one and not more than five persons.

The prior art discloses a wide variety of fan driven air fresheners. The prior art attempts to overcome several disadvantage of air fresheners. One disadvantage, as pointed out by Homg is that commercially available air fresheners commonly use a container to carry a liquid chemical or solid spices, permitting the smell of the liquid chemical or solid spices to be released into the air for freshening the room, motor vehicle, etc. When a liquid chemical is used for releasing a smell for freshening the air, it will be splashed over the surrounding areas when the container is shaken heavily. Therefore, a need exists for a device that will not allow liquid or solid scent material to be spilled or splashed into the room or area in which the device is to be used.

An examination of the prior shows that none of the devices is truly automatic. In other words, timers and on-off switches have been provided but none of the prior art devices introduces scent into the air of the motor vehicle or habitable structure at the same time as air is forced through the air-conditioning system into the passenger compartment of the motor vehicle or into the rooms of the habitable structure with vents for the air conditioning system. Therefore, a need exists for a device that can will introduce scent automatically at the same time that air is being introduced into the passenger compartment of a motor vehicle or into the room of a habitable structure by the existing air conditioning system.

All of the prior art is specific for the one area in which scent is to be introduced. The device must be positioned in the room or space where the device is to function. Thus based on the prior art a device is necessary for each room or the device must be moved from room to room. An additional disadvantage is that the device is visible in the room. Therefore, a need exists for a device that can introduce scent directly into the air conditioning duct of a motor vehicle or habitable dwelling so that the device will not be visible and it will not be necessary to install a separate device in each room or area into which a freshening scent is to be introduced.

Finally, a need exists for a device that can automatically provide a scent into the air of a motor vehicle or habitable structure without the need for frequent replenishment of the scent producing material.

SUMMARY OF THE INVENTION

The present invention is an automatic air scenting system that introduces a variety of pre-selectable scents into the heating/air-conditioning duct of a motor vehicle or habitable structure comprising a perforated housing, an electric fan for drawing air through the perforated housing, a container of compressed fiber blocks soaked in a scented oil based liquid positioned within the perforated housing, and a hose connecting the housing to the duct of the heating/air conditioning system whereby the fan forces the accumulated scent through the hose into the duct. Automatic functioning is obtained by connecting the fan power lines to the on/off switch and thermostat wiring of the heating/air-conditioning system.

BRIEF DESCRIPTION OF THE DRAWINGS

The apparatus of the invention is further described and explained in relation to the following figures of the drawings wherein:

FIG. 3 is an exploded view of the apparatus.

DESCRIPTION OF PREFERRED EMBODIMENTS

Figure 1:
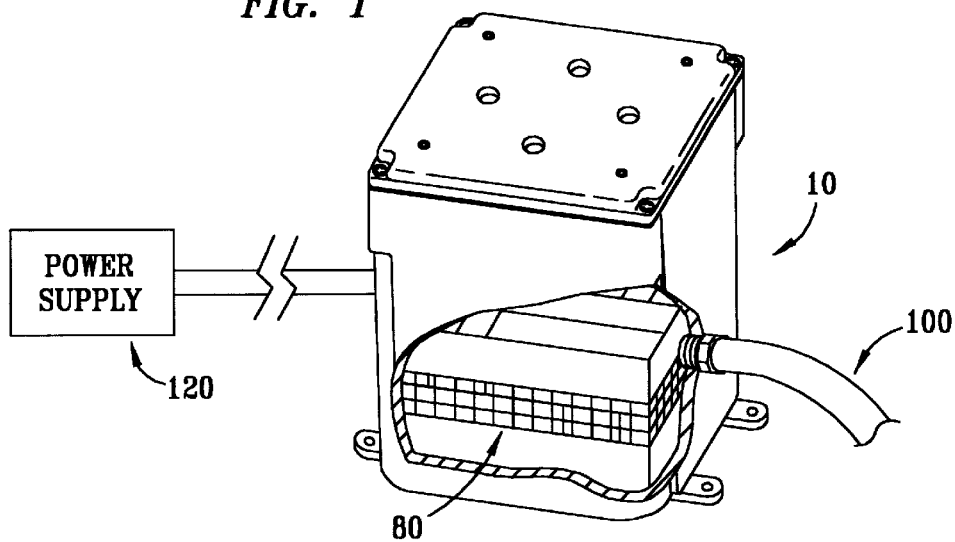
FIG. 1 is a view of the assembled apparatus with a cutaway view into the interior.

In the discussion of the figures, the same numbers will be used to refer to the same or similar components throughout. According to the present invention, FIG. 1 depicts a view of the assembled apparatus for introducing a plurality of scents into the duct of the heating/air conditioning system of a vehicle or habitable structure which consists of four main elements, a housing element 10, a canister element 80, a connecting element 100 and an external power supply 120. Air is forced through housing element 10 to carry scent from canister element 80 into the air passage or duct of the existing air conditioning system. In the preferred embodiment the power supply 120 will be the existing power supply which powers the existing air conditioning system; however, appropriate standard batteries may be adapted for independent use. Power supply 120 is controlled by an existing on/off switch and existing thermostat.

Figure 2:
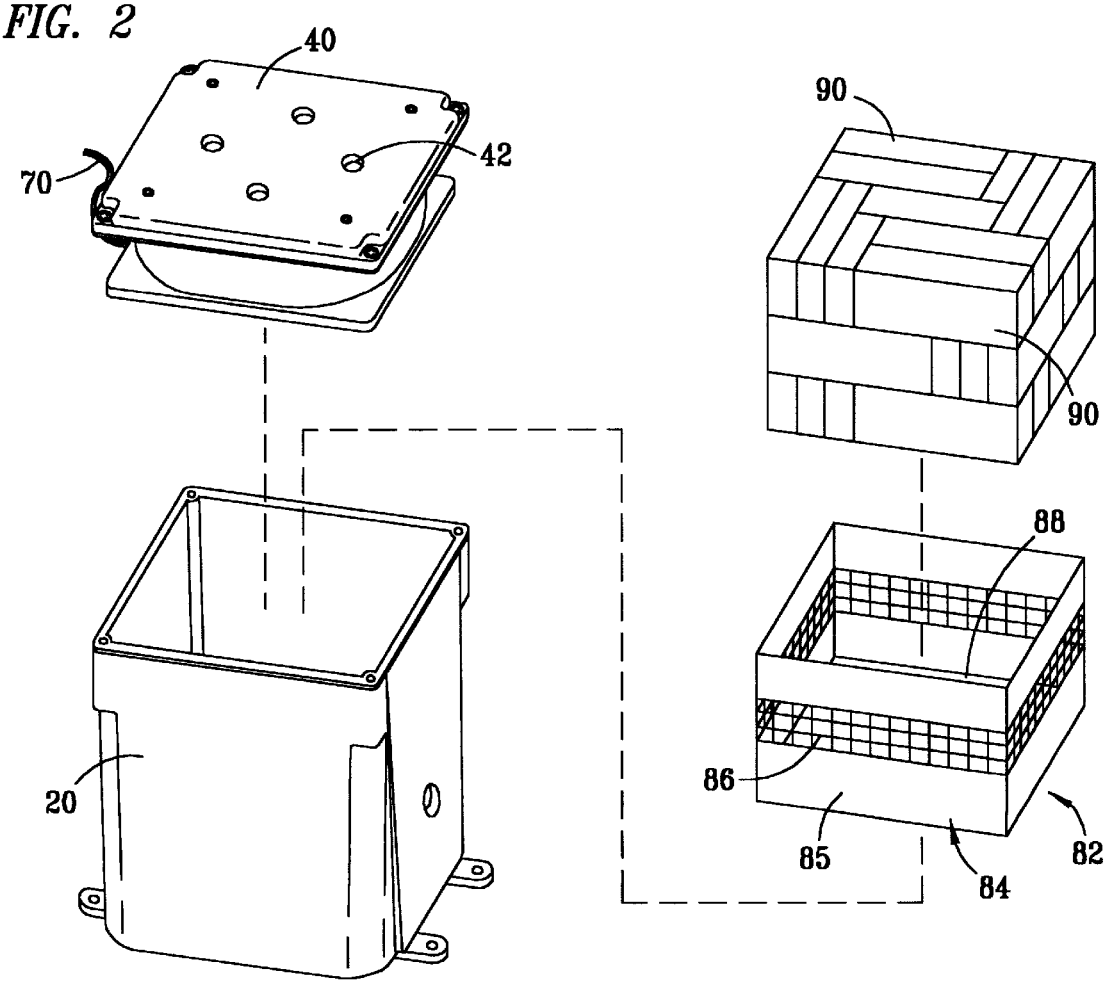
FIG. 2 is an exploded view of a partially assembled apparatus.

FIG. 2 shows housing element 10 opened into its two main components, container 20 and lid 40 to reveal canister element 80 which consists of cage 82 and blocks 90. Canister element 80 is the scent producing part of the apparatus. In the preferred embodiment Blocks 90 are commercially available blocks of compressed vegetable fiber such as are available from the California Scent company, 3034 South Orange Avenue, Santa Ana, Calif. 92707 under the trade name "California Spill Proof Organic Air Freshener." The compressed vegetable fiber blocks may contain some scent when obtained from the manufacturer; however, for use in the disclosed invention the blocks are further soaked in mineral oil to which any desired commercially available scent has been added because the soaking in the scented oil based liquid prolongs the life of the blocks in emitting scent. Blocks 90 may also be made from compressed cardboard where the cardboard has been shredded or ground into particles, mixed with an adhesive and pressed into blocks. Preferably the shredded cardboard would be compressed until not capable of further compression and the material becomes substantially non-compressible. Blocks 90 can also be made from joint expansion board such as Georgia Pacific ½" by 4" by 5' boards, Part No. 101584, where the boards can be cut into blocks and the inner fibrous material is capable of absorbing the scented oil based liquid. The blocks made from joint expansion board are capable of further compression and while suitable, will not emit scent as long as the vegetable fiber blocks which are substantially non-compressible. Blocks 90 can also be made from any suitable fibrous material with a porosity capable of absorbing a scent bearing oil based liquid such as mineral oil and the most desirable would be those that can be made to be substantially non-compressible. Blocks 90 are approximately 1 inch high, 1 inch wide and 2 inches long; however, blocks 90 can be made in any size. The preferred embodiment is the 1 inch by 1 inch by 2 inch size because that size is best for absorbing the scent bearing oil based liquid. Blocks 90 are soaked in an oil based liquid either by placing them in a receptacle holding the oil based liquid or blocks 90 are placed within canister 80 and canister 80 with blocks 90 stacked inside is placed into a receptacle holding the oil based liquid. A standard five gallon can is the easiest receptacle to use when soaking blocks 90 in the oil based liquid. In the preferred embodiment, the oil based liquid is mineral oil and any desired commercially available scent is added to the mineral oil to produce the scented oil based liquid. Blocks 90 should be soaked for approximately one hour. When the blocks 90 have become saturated or fully impregnated, they are placed in cage 82, or if soaked while in cage 82, cage 82 containing blocks 90 is lifted and placed inside container 20. Blocks 90 are packed tightly inside cage 82. Packing blocks 90 tightly slows the evaporation of the scented oil based liquid. One canister of properly soaked blocks 90 stacked within cage 82 can effectively emit scent for approximately four months. The recommended interval for re-soaking the blocks in scent bearing oil based liquid is 60 days. However, an optional procedure allows extending the time the blocks can be used without removing them for re-soaking. A plastic squeeze bottle with a nozzle is filled with the scent bearing oil based liquid and the nozzle is placed into one of air holes 42 and the scent bearing oil based liquid is squeezed from the bottle and allowed to drop onto blocks 90 inside container 20.

Cage 82 has floor 88 and plurality of walls 84. Floor 88 and walls 84 can be made from wire mesh 86 or a combination of wire mesh 86 and sheet metal 85. Cage 82 as shown is made by folding sheet metal 85 over wire mesh 86 to stiffen walls 84 and floor 88. Walls 84 and floor 88 are fixedly engaged to each other by soldering or rivets. Additionally floor 88 and walls 84 can be made of molded plastic wherein floor 88 and walls 84 are perforated with a plurality of holes allowing the passage of oil based liquid through canister cage 82. When the properly soaked blocks 90 are stacked within cage 82, canister element 80 is complete and ready for installation within container 20.

FIG. 3, shows the apparatus in a complete exploded view. Each item shall be discussed from top to bottom. Lid 40 contains a plurality of air holes 42, a plurality of fan mounting holes 48, and a plurality of lid mounting holes 49. Lid 40 has lid first side 44 and lid second side 46. Lid second side 46 has an optional annular edge 45. Lid 40 is made from strong hard plastic. Gasket 50 slides over annular edge 45 of lid second side 46. If lid 40 does not have annular edge 45, then gasket 50 is placed on lid second side 46 and lid mounting holes 49 are lined up with gasket mounting holes 52. Fan 60 is attached to lid second side 46 by means of second fasteners 14 placed in fan mounting holes 48 to engage mounting holes 61 in casing 68 of fan 60.

Fan 60 comprises a plurality of blades 62, motor 64 and casing 68 for blades 62 and motor 64. Motor 64 is electrically energizable and contained within casing 68 and connected to power supply 120 by wires 70. Blades 62 are connected to motor 64 such that operation of motor 64 creates air flow into housing element 10 through air holes 42 over and around canister element 80 and through connecting element 100 into the existing duct 130. There can be any number of blades 62 radiating from hub 63 connected to motor 64.

Wires 70 are connected to motor 64 by any standard means such as soldering, screws or contact clips. In the preferred embodiment for automotive installation, fan 60 is a Radio Shack, 12 V DC Brushless Fan, Cat. No. 273-243B .16A 1.9W. In the preferred embodiment for installation in habitable structure, fan 60 is a 120 V AC 60 Hz 22 W No. E89061 Radio Shack cooling fan Cat. 273-241C.

Canister element 80 is described above in the description of FIG. 2.

Container 20 is made from the same strong hard material as lid 40. The preferred embodiment utilizes plastic that is rigid and impact resistant. In the preferred embodiment, container 20 is injection molded in one piece. However, container 20 can also be assembled from several pieces. Container 20 comprises base 28 with rectangular planar first side 22, rectangular planar second side 24 and a plurality of rectangular planar third sides 26. First side 22 is a rectangular planar wall containing aperture 23 for receiving connector 100, second side 24 is a rectangular planar wall containing aperture 25 for receiving electrical wires 70. Third side 26 is a rectangular planar wall without any apertures. First side 22, second side 24 and a plurality of third sides 26 are fixedly connected to each other and to base 28 to form container 20. First side 22, second side 24 and third sides 26 extend upward perpendicular to base 28 to define an enclosed interior space. First side 22, second side 24 and third side 26 each have a top end and a bottom end where the bottom ends are fixedly engaged to base 28. The top ends of first side 22, second side 24 and third sides 26 define the opening of container 20 and together comprise edge 30. First side 22, second side 24, third sides 26 and base 28 can be made from molded plastic and therefore joined without any seams. If container 20 is made from metal then the sides and the base can be connected by welding. Evaporation of the scent bearing oil based liquid from blocks 90 is not appreciably affected by air holes 42; however, if the sides of container 20 are not sealed either by being formed through injection molding if plastic or by welding if made of metal, the period of time in between soaking blocks 90 will be reduced to a much shorter period of time such as 2–3 days.

Before attaching lid 40 to container 20, wires 70 are passed through aperture 25 of second side 24 of container element 20 and blocks 90 are placed within canister 80 and canister 80 is positioned upright on base 28 of container 20. Lid 40 is then positioned above container 20 and pressed down onto container so that annular edge 45 and gasket 50 engage edge 30 of container 20. First fasteners 12 are then inserted into receiving holes 49 to removably engage lid 40 to container 20. In the preferred embodiment first fasteners 12 are screws. Gasket 50 insures that there is a good seal between lid 40 and container 20. The only access for air into housing element 10 is through the plurality of holes 42.

Connecting element 100 consists of connector fitting 110 and hose 104. Connector fitting 110 has connector fitting first end 112, connector fitting second end 114 and connector fitting middle section 116. Connector fitting first end 112 is threaded so that it mates with aperture 23 in container first side 22. Connector fitting second end 114 has a friction fitting for receiving first end 102 of hose 100. Second end 104 of hose 100 is slidingly engaged with connector fitting second end 114 of another connector 110 and connector fitting first end 112 is engaged with aperture 122 in duct 130 Installation of connecting element 100 requires making aperture 122 in duct 130 by drilling, cutting or auguring. Hose 104 is approximately 1 to 2 feet in length. Hose 104 can be as long as 10 feet. However, after 10 feet the effectiveness of fan 60 in driving the air bearing the scent from housing element 10 through hose 104 and into ductwork 130 is diminished. Hose 104 is made of plastic or polyurethane and has an outside diameter of approximately ½" and an inside diameter of ⁶⁄₁₆" to ¼." Any commercially available plastic or polyurethane hose of approximately ½" diameter is suitable. Aperture 122 is approximately ½ inch in diameter and is adapted for receiving connector fitting first end 112. An optional procedure is to place a washer and nut on the threads of connector fitting first end 112 on the inside of duct 130 so that connector fitting 110 will not come loose from duct 130.

Wires 70 are connected to power supply 120 having an on/off switch and a thermostat of the heating air/conditioning system so that when the switch or thermostat is turned on power is sent to fan 62, air is drawn into housing element 10 where scent is accumulating and the air and scent are forced through hose 104 into duct 130 of the existing heating/air conditioning system. Alternatively, wires 70 are connected to a switch on a wall connected to the existing heating/air conditioning system or to the main heating/air conditioning thermostat.

Housing element 10 is mounted in the motor vehicle or habitable structure by means of brackets 29 fixedly engaged to the base of the container element. Brackets 29 contain holes for receiving third fasteners 16 which connect housing element 10 to the motor vehicle or habitable structure.

The above described invention meets the needs previously identified because canister element 80 is completely contained with housing element 10, housing element 10 does not allow scented liquids or solids to be splashed into the room or area to be freshened. Because housing element 10 is directly linked to power supply 120 the apparatus is truly automatic in that it forces scented air into duct 130 every time the existing fan driven air conditioning system is turned on either manually or by the thermostat. Finally, because housing element 10 is directly connected to duct 130 by connecting element 100 only one apparatus is necessary in order to freshen all of the room of a habitable structure.

The invention further discloses the method of introducing an air freshening scent into the passenger compartment of a motor vehicle or into the rooms of a habitable structure comprising the steps of selecting an oil based liquid with the desired scent; placing the selected oil based liquid in a vessel; placing blocks of compressed cardboard into the container containing the scent bearing oil based liquid; soaking the blocks in the container of scent bearing oil based liquid until the blocks are saturated or fully impregnated; removing the blocks and placing them in a cage; placing the cage inside a perforated housing unit containing an electrically energizable fan; connecting the fan to the power supply of the heating air conditioning system; connecting the perforated housing unit to the heating air conditioning system by means of a hose and connectors.

Those skilled in the art should appreciate that the conception and the specific embodiment disclosed may be readily utilized as a basis for modifying or designing other structures for carrying out the same purposes of the present invention. Those skilled in the art should also realize that such equivalent constructions do not depart for the spirit and scope of the invention as set forth in the appended claims. Other alternatives and modifications of the invention will likewise become apparent to those of ordinary skill in the art upon reading the present disclosure, and it is intended that the scope of the invention disclosed herein be limited only by the broadest interpretation of the appended claims to which the inventor is legally entitled.

What is claimed:

1. An apparatus for introducing a pre-selectable plurality of scents obtained from a plurality of scented oil based liquids into the duct of an existing electrically energizable heating/air conditioning system of a motor vehicle or habitable structure electrically connected to a power supply wherein said heating/air conditioning system is controlled by an on/off switch or thermostat comprising:

a housing element comprising a lid having a plurality of air holes and a top and a bottom, a container, and a fan fixedly engaged to said bottom of said lid wherein said fan is electrically energizable and electrically connected to said on/off switch or thermostat;

a canister element removably positioned within the housing element comprising a cage and a plurality of blocks wherein the blocks are impregnated with a scented oil based liquid; and a connecting element removably engaged to said housing element and said duct; wherein said fan upon being electrically energized causes air to be drawn through the plurality of apertures in said lid so that the air passes over the blocks and is forced through the connecting element into the duct.

2. The apparatus of claim 1 wherein said blocks are removably afixed within said cage.

3. The apparatus of claim 1 further comprising a gasket positioned between the lid and the container.

4. An apparatus for introducing a pre-selectable plurality of scents obtained from a plurality of scented oil based liquids into the duct of an existing electrically energizable heating/air conditioning system of a motor vehicle or habitable structure electrically connected to a power supply wherein said heating/air conditioning system is controlled by an on/off switch or thermostat comprising:

a housing element comprising a lid and a container, said lid further comprising a plurality of air holes, a plurality of lid mounting holes, a plurality of fan mounting holes and a top and a bottom and said container further comprising a base, a first side, a second side, and a plurality of third sides, said first side having a connector aperture for receiving a first connector and said second side having a plurality of wire apertures for receiving a plurality of wires;

a plurality of brackets affixed to said container;

a gasket positioned between the lid and the container;

a fan comprising, a motor connected to a casing wherein said casing is removably affixed to said bottom of said lid, a plurality of blades rotatably affixed to said motor, and the plurality of wires having a first end and second end, said first end connected to said motor and said second end connected to said on/off switch or thermostat;

a canister element removably positioned within the housing element comprising a cage and a plurality of blocks wherein the blocks are impregnated with a scented oil based liquid;

a connecting element comprising a hose with a container end and a duct end, a first connector fitting and a second connector fitting, wherein said first connector fitting is removably engaged to said housing element and to the container end of said hose and said second connector fitting is removably engaged to said duct end of said hose and to said duct;

wherein scent from the blocks is accumulated within the housing element and carried to the duct by air driven by the fan;

wherein said fan is electrically energizable; and wherein said fan upon being electrically energized causes air to be drawn through a plurality of apertures in said lid so that the air passes over the blocks and is forced through the connecting element into the duct.

5. A method of introducing a pre-selectable plurality of scents obtained from a plurality of scented oil based liquids into the air duct of an existing electrically energizable heating/air conditioning system of a motor vehicle or habitable structure controlled by an on/off switch or thermostat comprising:

selecting the scented oil based liquid with the desired scent;

pouring the selected scented oil based liquid into a vessel;

placing blocks into the vessel containing the scented oil based liquid;

soaking the blocks in the vessel containing the scented oil based liquid;

removing the blocks and placing them in a cage;

placing the cage inside a container;

removably engaging said lid to said container by means of a plurality of fasteners;

connecting a plurality of wires to the fan and to the on/off switch or thermostat of the heating/air conditioning system so that the fan will be electrically energized when the on/off switch or the thermostat provides power to the heating/air conditioning system;

creating an aperture in the duct of the existing heating air conditioning system for receiving a connector fitting; and connecting the housing element to the aperture by means of a connecting element comprising a hose and a plurality of connector fittings.

6. The method of claim 5 wherein scent bearing oil based liquid is poured into the housing element by means of squeezable plastic bottle containing scent bearing oil based liquid, said squeezable plastic bottle having a nozzle where said nozzle is placed in an aperture in said lid, said bottle is squeezed to cause scent bearing oil based liquid to drip into the housing element and fall upon the blocks contained therein.

* * * * *